(12) United States Patent
Harada et al.

(10) Patent No.: US 7,049,458 B2
(45) Date of Patent: May 23, 2006

(54) PROCESS FOR PRODUCING β-KETONITRILE COMPOUND

(75) Inventors: Katsumasa Harada, Yamaguchi (JP); Shigeyoshi Nishino, Yamaguchi (JP); Kenji Hirotsu, Yamaguchi (JP); Akira Nakamura, Yamaguchi (JP); Takashi Harada, Yamaguchi (JP)

(73) Assignee: Ube Industries, Ltd. (JP)

( * ) Notice: Subject to any disclaimer, the term of this patent is extended or adjusted under 35 U.S.C. 154(b) by 145 days.

(21) Appl. No.: 10/451,280

(22) PCT Filed: Dec. 25, 2001

(86) PCT No.: PCT/JP01/11390

§ 371 (c)(1), (2), (4) Date: Jun. 23, 2003

(87) PCT Pub. No.: WO02/051798

PCT Pub. Date: Jul. 4, 2002

(65) Prior Publication Data
US 2004/0068136 A1   Apr. 8, 2004

(30) Foreign Application Priority Data
Dec. 22, 2000  (JP) .............................. 2000-389776
Jan. 25, 2001  (JP) .............................. 2001-016700

(51) Int. Cl.
*C07C 255/03*  (2006.01)

(52) U.S. Cl. ..................................... 558/405

(58) Field of Classification Search ................ 558/405
See application file for complete search history.

(56) References Cited

U.S. PATENT DOCUMENTS 4,945,177 A  *  7/1990  Krause et al. .............. 558/405

FOREIGN PATENT DOCUMENTS

| EP | 89011 A1 | 9/1983 |
|---|---|---|
| EP | 623590 A1 | 11/1994 |
| GB | 787858 A | 12/1957 |

\* cited by examiner

*Primary Examiner*—Johann Richter
*Assistant Examiner*—Ebenezer Sackey
(74) *Attorney, Agent, or Firm*—Nixon Peabody LLP; Jeffrey L. Costellia

(57) ABSTRACT

A process comprising reacting an aliphatic carboxylic ester compound with acetonitrile in the presence of a metal alkoxide to yield a metal salt of a β-ketonitrile compound, subsequently transferring the salt to an aqueous medium, and neutralizing the solution to obtain the β-ketonitrile compound in a free state, wherein a water-immisible organic solvent and water are added to the reaction mixture containing the β-ketonitrile compound metal salt yielded to transfer the metal salt to the water, the resultant aqueous solution of the β-ketonitrile compound metal salt is separated from the organic solvent by phase separation or another technique and then neutralized, and the resultant free β-ketonitrile compound is taken out by extraction with an organic solvent.

8 Claims, No Drawings

PROCESS FOR PRODUCING β-KETONITRILE COMPOUND

TECHNICAL FIELD

The present invention relates to a process for producing a β-ketonitrile compound from an aliphatic carboxylic acid ester compound. The β-ketonitrile compound is useful as a starting compound for preparing pharmaceutically active compounds as well as agriculture chemicals.

BACKGROUND ART

As for the process for producing a β-ketonitrile compound by reacting an aliphatic carboxylic acid ester compound in the presence of a metal alkoxide, J. Am. Chem. Soc., 56, 1171 (1934) discloses a reaction between ethyl isobutylate and acetonitrile in the presence of sodium ethoxide, and Japanese Patent Provisional Publication No. 6-312966 discloses a reaction between an acetic acid ester and acetonitile in the presence of an alkali alcolate.

According to the study performed by the present inventors, it has been revealed that the reactions disclosed in the prior art publications yield by-products such as 3-oxybutyronitrile and compounds having pyrimidine nucleus in addition to the desired product of β-ketonitrile compound. Thus, the known processes could not yield the β-ketonitrile compound of a high purity in a good yield.

It is an object of the present invention to provide an industrially applicable process for producing a β-ketonitrile compound of high purity in a good yield from an easily available aliphatic carboxylic acid ester compound.

DISCLOSURE OF THE INVENTION

The present invention resides in a process for producing a β-ketonitrile compound having the formula. (3):

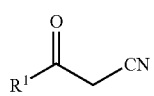

(3)

in which $R^1$ represents an aliphatic group which comprises the steps of:

(A) reacting an aliphatic carboxylic acid ester compound having the formula (1):

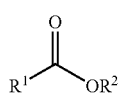

(1)

in which $R^1$ has the same meaning as defined above, and $R^2$ is a group which does not participate in the instant reaction, with acetonitrile in the presence of a metal alkoxide having a metal atom of X to give a reaction mixture containing a metal salt of a β-ketonitrile compound having the formula (2):

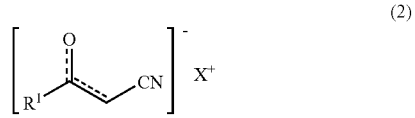

(2)

in which $R^1$ and X have the same meanings as defined above;

(B) adding a water-immiscible organic solvent and water to the reaction mixture, mixing them, and separating the aqueous solution containing the metal salt of β-ketonitrile compound; and (C) neutralizing the aqueous solution containing the metal salt of β-ketonitrile compound by addition of an acid and extracting a free β-ketonitrile compound with an organic solvent.

DETAILED DESCRIPTION OF THE INVENTION

The present invention comprises the following three steps:

Step (A): a step of reaction for obtaining a reaction mixture containing a metal salt of a β-ketonitrile compound by reacting an aliphatic carboxylic acid ester compound and acetonitrile in the presence of a metal alkoxide;

Step (B): a step of separation for obtaining an aqueous solution containing the metal salt of β-ketonitrile compound by mixing the reaction mixture with water and a water-immiscible organic solvent and separating an aqueous solution from an organic solvent phase; and Step (C): a step of neutralization-extraction for obtaining a free β-ketonitrile compound by neutralizing the aqueous solution containing the metal salt of β-ketonitrile compound by addition of an acid and then subjecting the neutralized mixture to extraction procedure using an organic solvent.

The above-mentioned three steps are described below in more detail.

(A) Step of Reaction

In this step, an aliphatic carboxylic acid ester compound and acetonitrile are reacted in the presence of a metal alkoxide to prepare a metal salt of a β-ketonitrile compound.

The aliphatic carboxylic acid ester compound employed in this step is represented by the aforementioned formula (1). In the formula (1), $R^1$ is an aliphatic group such as an alkyl group, a cycloalkyl group, or an aralkyl group. The alkyl group preferably has 1 to 10 carbon atoms. Examples of the alkyl groups include methyl, ethyl, propyl, butyl, pentyl, hexyl, heptyl, octyl, nonyl, and decyl. These groups may be any isomers of optionally selected forms. The cycloalkyl group preferably has 3 to 7 carbon atoms. Examples of the cycloalkyl groups include cyclopropyl, cyclobutyl, cyclopentyl, cyclohexyl, and cycloheptyl. These groups may be any isomers of optionally selected forms. The aralkyl group preferably has 7 to 10 carbon atoms. Examples of the aralkyl groups include benzyl, phenethyl, phenylpropyl, and phenylbutyl. These groups may be any isomers of optionally selected forms.

In the formula (1), $R^2$ is a group which is inert in the reaction and typically is a hydrocarbyl group. Examples include an alkyl group, a cycloalkyl group, an aralkyl group, and an aryl group. The alkyl group preferably has 1 to 10 carbon atoms. Examples of the alkyl groups include methyl, ethyl, propyl, butyl, pentyl, hexyl, heptyl, octyl, nonyl, and decyl. These groups may be any isomers of optionally selected forms. The cycloalkyl group preferably has 3 to 7 carbon atoms. Examples of the cycloalkyl groups include cyclopropyl, cyclobutyl, cyclopentyl, cyclohexyl, and cycloheptyl. These groups may be any isomers of optionally selected forms. The aralkyl group preferably has 7 to 10 carbon atoms. Examples of the aralkyl groups include benzyl, phenethyl, phenylpropyl, and phenylbutyl. These groups may be any isomers of optionally selected forms. The aryl group preferably has 6 to 14 carbon atoms. Examples of the aryl groups include phenyl, tolyl, naphthyl, and anthryl. These groups may be any isomers of optionally selected forms.

The metal atom (X) of the metal alkoxide can be an atom of Group IA such as lithium, sodium, or potassium, an atom of Group 2A such as magnesium or calcium, or an atom of Group 3B such as aluminum. These Groups are described in Dictionary of Physics and Chemistry, 4th ed. (Iwanami Publishing). Examples of the metal alkoxides include Group 1A metals alkoxides such as lithium methoxide, sodium methoxide, potassium methoxide, sodium ethoxide, potassium ethoxide, and potassium t-butoxide, Group 2A metal alkoxides such as magnesium methoxide and calcium methoxide, and Group 3B metal alkoxides such as aluminum isopropoxide. Preferred is a sodium alkoxide, and most preferred is sodium methoxide.

The metal alkoxide can be employed in an amount of, preferably 1.0 to 2.5 moles, more preferably 1.1 to 2.0 moles, per one mole of the aliphatic carboxylic acid ester compound. The metal alkoxides can be employed singly or in combination of two or more.

Acetonitrile can be employed in the reaction in an amount of, preferably 1.1 to 2.5 moles, more preferably 1.2 to 2.0 moles, per one mole of the aliphatic carboxylic acid ester compound.

The reaction is preferably carried out in the presence of not only the acetonitrile (i.e., starting compound which also functions as an organic solvent) but also a aprotic polar organic solvent. There are no specific limitations with respect to the aprotic polar organic solvent, so long as it does not participate in the reaction. Preferably, it has a relative dielectric constant (relative permittivity) in the range of 30 to 50 at a temperature range of 20 to 25° C. (at an arbitrary temperature in this range). Examples of these organic solvents include sulfoxides such as dimethyl sulfoxide, sulfones such as sulfolane, ureas such as N,N'-dimethylimidazolidinone, and amides such as N,N-dimethylacetamide. Preferred are dimethyl sulfoxide and N,N'-dimethylimidazolidinone. The relative dielectric constants are described in "Handbook of Chemistry (II), basic edition, 4th ed." (Maruzen Publishing), "Solvent Handbook, 1st ed." (Koudansha Scientific), and "13700 Commercially Available Chemical Products" (Chemical Industry Daily, Ltd.).

The aprotic polar organic solvent can be employed in an amount of, preferably not more than 10 weight parts, more preferably 0.5 to 10 weight parts, most preferably 0.75 to 5 weight parts, per one weight part of the aliphatic carboxylic acid ester compound. These organic solvents can be used singly or in combination of two or more.

The reaction can be carried out, for instance, under inert gas atmosphere, by mixing a metal alkoxide, an aliphatic carboxylic acid ester compound, acetonitrile, and optionally a aprotic polar organic solvent, and then heating the resulting mixture preferably to 50–110° C., more preferably 60 to 100° C. There is no limitation with respect to the reaction pressure.

(B) Step of Separation

The step of separation can be carried out by mixing the reaction mixture containing β-ketonitrile compound [which was obtained in the step (A)] with water and a water-immiscible organic solvent and subsequently separating an aqueous solution (aqueous phase) containing the metal salt of β-ketonitrile compound from an organic phase by means of, for instance, phase separation. Examples of the organic solvents include ethers such as diethyl ether and di-isopropyl ether, aromatic hydrocarbons such as benzene and toluene, halogenated aromatic hydrocarbons such as chlorobenzene and dichlorobenzene, and esters such as ethyl acetate and butyl acetate. Preferred are ethers and aromatic hydrocarbons, and more preferred are aromatic hydrocarbons. These organic solvents can be used singly or in combination of two or more. If desired, a lower alcohol can be added to enhance fluidity, under the condition that the addition of a lower alcohol does not disturb the phase separation.

The organic solvent is preferably employed in such an amount as to not disturb the phase separation between the organic phase and aqueous phase. For example, the organic solvent can be used in an amount of, preferably 0.5 to 30 volume parts, more preferably 1 to 10 volume parts, per one part of the aliphatic carboxylic acid ester compound.

Water is used in such an amount as to completely dissolve the resulting metal salt of β-ketonitrile compound. For example, water can be used in an amount of, preferably 1 to 50 volume parts, more preferably 2 to 30 volume parts, per one volume part of the aliphatic carboxylic acid ester compound.

The step of phase separation is preferably carried out by first adding the organic solvent to the reaction liquid (reaction mixture) so as to enhance fluidity and then adding water under stirring. In this procedure, the reaction liquid is preferably kept at a temperature in the range of 10 to 50° C., more preferably 20 to 40° C. This procedure is favorably adopted for keeping the reaction liquid from solidification.

(C) Step of Neutralization-Extraction

The step of neutralization-extraction is carried out for adding an acid to the aqueous solution containing a metal salt of β-ketonitrile compound (which was obtained in the step of separation) for neutralization and then extracting the resulting free β-ketonitrile compound with an organic solvent. Examples of the acids employable in this step include hydrochloric acid, sulfuric acid, nitric acid, phosphoric acid, methanesulfonic acid, acetic acid, and ammonium chloride (or aqueous ammonium chloride). Preferred are hydrochloric acid, sulfuric acid, and ammonium chloride (or aqueous ammonium chloride). The acid can be added in such an amount as to make pH of the aqueous solution to preferably 6–10. It is desired that the addition of acid is carried out to keep the temperature of the aqueous solution at 0–50° C.

There are no specific limitations with respect to the organic solvent employed in the step of neutralization-extraction, so long as it can extract the free β-ketonitrile compound from the aqueous solution. The organic solvent preferably is immiscible with water. Examples of the organic solvents include aromatic hydrocarbons such as benzene and toluene, esters. such as ethyl acetate and butyl acetate, and halogenated hydrocarbons such as dichloromethane and dichloroethane. Preferred are aromatic hydrocarbons and acetic acid esters. More preferred are aromatic hydrocarbons.

The organic solvent can be employed in such an amount as to extract the free β-ketonitrile compound produced in the aqueous solution by neutralization.

By the step of neutralization-extraction, a free β-ketonitrile compound is obtained with a high purity in the form of an organic solvent solution. The resulting product or solution can be further subjected to conventional after-treatment procedures such as concentration, distillation, crystallization, recrystallization, or column chromatography. It should be noted that the β-ketonitrile compound is unstable on heating. Therefore, when the distillation is carried out, a thin layer distillation apparatus or a flow-down film distillation apparatus is preferably employed.

The present invention is further described by the following non-limiting examples.

EXAMPLE 1

Preparation of 3-cyclopropyl-3-oxopropio-nitrile

In a glass flask (inner volume: 1,000 mL) equipped with a stirrer, a thermometer, a dropping funnel and a reflux condenser were placed 81.0 g (1.5 mol) of sodium methoxide, 100.0 g (1.0 mol) of methyl cyclopropanecarboxylate and 61.5 g (1.5 mol) of acetonitrile under nitrogen atmosphere. The mixture was heated under reflux at 82° C. for 6 hours. After the reaction was complete, 400 mL of toluene was added to the reaction mixture, and the resulting mixture was cooled to room temperature. To the cooled mixture was dropwise added 200 mL of water under stirring, keeping the temperature of the mixture at 30° C. or lower. Thus produced aqueous portion was taken out.

Subsequently, to the aqueous portion was added 135 mL (1.6 mol) of hydrochloric acid (12 mol/L), while chilling the aqueous portion in an ice bath. After the aqueous solution became to have pH 7.0, the solution was subjected to extraction using three portions of 200 mL toluene. The toluene portions were combined and washed with 50 mL of an aqueous saturated sodium hydrogen carbonate solution and then dried over magnesium sulfate. The toluene solution was filtered and then analyzed by high performance liquid chromatography (absolute quantitative analysis). It was confirmed that the following products were produced:

3-cyclopropyl-3-oxopropionitrile (desired product):
 81.1 g (yield: 74%)
3-oxobutyronitrile (by-product):
 0.45 g (0.55 wt. % of the desired product)
Compound having pyrimidine nucleus (by-product):
 0.15 g (0.18 wt. % of the desired product).

The filtered toluene solution was concentrated under reduced pressure to give 80.2 g (isolation yield: 72%) of 3-cyclopropyl-3-oxopropionitrile (purity: 98.2%) as yellow liquid. The purity was determined by high performance liquid chromatography.

The obtained 3-cyclopropyl-3-oxopropionitrile had the following characteristics:
 EI-MS (m/e) : 69 (M-CH$_2$CN), CI-MS (m/e): 110 (M+1)
 IR (cm$^{-1}$, liquid film): 3200–2900, 2261, 1713, 1389, 1073, 953
 $^1$H-NMR (CDCl$_3$, δ(ppm)): 1.05–1.15 (2H, m), 1.18–1.25 (2H, m), 2.06–2.15 (1H, m), 3.64 (2H, s).

REFERENCE EXAMPLE 1

Preparation of 3-cyclopropyl-3-oxopropionitrile
(with No Phase Separation Step)

In the reaction apparatus described in Example 1 were placed 81.0 g (1.5 mol) of sodium methoxide, 100.0 g (1.0 mol) of methyl cyclopropanecarboxylate and 61.5 g (1.5 mol) of acetonitrile under nitrogen atmosphere. The mixture was heated under reflux at 82° C. for 6 hours. After the reaction was complete, 400 mL of toluene was added to the reaction mixture, and the resulting mixture was cooled to room temperature. To the cooled mixture were added 280 mL (1.7 mol) of hydrochloric acid (6 mol/L) and 100 mL of water, keeping the temperature of the resulting mixture at 30° C. or lower. After the reaction mixture became to have pH 2.0, the mixture was extracted with 3 portions of 200 mL toluene. The toluene portions were combined and washed with 50 mL of an aqueous saturated sodium hydrogen carbonate solution and then dried over magnesium sulfate. The toluene solution was filtered and then analyzed by high performance liquid chromatography (absolute quantitative analysis). It was confirmed that the following products were produced:

3-cyclopropyl-3-oxopropionitrile (desired product):
 72.3 g (yield: 66%)
3-oxobutyronitrile (by-product):
 0.60 g (0.83 wt. % of the desired product)
Compound having pyrimidine nucleus (by-product):
 1.33 g (1.8 wt. % of the desired product).

The filtered toluene solution was concentrated under reduced pressure to give 77.2 g (isolation yield: 66%) of 3-cyclopropyl-3-oxopropionitrile (purity: 93.6%) as yellow liquid. The purity was determined by high performance liquid chromatography.

EXAMPLE 2

Preparation of 4-methyl-3-oxopentanenitrile

In the reaction apparatus described in Example 1 were placed 81.0 g (1.5 mol) of sodium methoxide, 102.1 g (1.0 mol) of methyl isobutylate, and 61.5 g (1.5 mol) of acetonitrile under nitrogen atmosphere. The mixture was. heated under reflux at 82° C. for 6 hours. After the reaction was complete, 400 mL of toluene was added to the reaction mixture, and the resulting mixture was cooled to room temperature. To the cooled mixture was dropwise added 200 mL of water under stirring, keeping the temperature of the mixture at 35° C. or lower. Thus produced aqueous portion was taken out.

Subsequently, to the aqueous portion was added 95 mL (1.1 mol) of hydrochloric acid (12 mol/L), while chilling the aqueous portion in an ice bath. After the aqueous solution became to have pH 7.7, the solution was subjected to extraction using three portions of 300 mL toluene. The toluene portions were combined and washed with 50 mL of an aqueous saturated sodium hydrogen carbonate solution and then dried over magnesium sulfate. The toluene solution was filtered and concentrated under reduced pressure to give 78.9 g (isolation yield: 70%) of 4-methyl-3-oxopentanenitrile (purity: 98.5%, according to area percentage determined by high performance liquid chromatography) as pale yellow liquid.

The obtained 4-methyl-3-oxopentanenitrile had the following characteristics:
 EI-MS (m/e): 71 (M-CH$_2$CN), CI-MS (m/e): 112 (M+1)
 IR (cm$^{-1}$, liquid film): 3700–3100, 3100–2800, 2263, 1725, 1468, 1389, 1306, 1048, 939
 $^1$H-NMR (CDCl$_3$, δ(ppm)): 1.18 (6H, d, J=6.8 Hz), 2.84 (1H, m), 3.94 (2H, s).

EXAMPLE 3

Preparation of 4,4-dimethyl-3-oxopentane-nitrile

In a glass flask (inner volume: 100 mL) equipped with a stirrer, a thermometer, a dropping funnel and a reflux condenser were placed 8.10 g (0.15 mol) of sodium methoxide, 11.62 g (0.1 mol) of methyl pivalate, and 6.15 g (0.15 mol) of acetonitrile under nitrogen atmosphere. The mixture was heated under reflux at 82° C. for 6 hours. After the reaction was complete, 40 mL of toluene was added to the reaction mixture, and the resulting mixture was cooled to room temperature. To the cooled mixture was dropwise added 45 mL of water under stirring, keeping the temperature of the mixture at 35° C. or lower. Thus produced aqueous portion was taken out.

Subsequently, to the aqueous portion was added 9.5 mL (0.11 mol) of hydrochloric acid (12 mol/L), while chilling the aqueous portion in an ice bath. After the aqueous solution became to have pH 7.7, the solution was subjected to extraction using three portions of 30 mL toluene. The toluene portions were combined and washed with 50 mL of an aqueous saturated sodium hydrogen carbonate solution and then dried over magnesium sulfate. The toluene solution was filtered and then analyzed by high performance liquid chromatography (absolute quantitative analysis). It was confirmed that the following products were produced:

4,4-dimethyl-3-oxopentanenitrile (desired product):
7.25 g (yield: 58%)
3-oxobutyronitrile (by-product):
0.01 g (0.20 wt. % of the desired product)
Compound having pyrimidine nucleus (by-product):
0.01 g (0.14 wt. % of the desired product).

The filtered toluene solution was concentrated under reduced pressure to give 7.21 g (isolation yield: 57%) of 4,4-dimethyl-3-oxopentanenitrile (purity: 98.4%, according to area percentage determined by high performance liquid chromatography) as pale yellow solid.

The obtained 4,4-dimethyl-3-oxopentanenitrile had the following characteristics:

EI-MS (m/e): 57 (M-COCH$_2$CN), CI-MS (m/e): 126 (M+1)
IR (cm$^{-1}$, liquid film): 3000–2800, 2266, 1721, 1485, 1391, 1325, 1067, 935
$^1$H-NMR (CDCl$_3$, δ(ppm)): 1.21 (9H, s), 3.70 (2H, s)
m.p.: 67.8–68.7° C.

REFERENCE EXAMPLE 2

Preparation of 4,4-dimethyl-3-oxopentanenitrile (with No Phase Separation Step)

In the reaction apparatus described in Example 3 were placed 8.10 g (0.15 mol) of sodium methoxide, 11.62 g (0.10 mol) of methyl pivalate, and 6.15 g (0.15 mol) of acetonitrile under nitrogen atmosphere. The mixture was heated under reflux at 82° C. for 6 hours. After the reaction was complete, 40 mL of toluene was added to the reaction mixture, and the resulting mixture was cooled to room temperature. To the cooled mixture were added 28 mL (0.17 mol) of hydrochloric acid (6 mol/L) and 10 mL of water, keeping the temperature of the resulting mixture at 30° C. or lower. After the reaction mixture became to have pH 2.0, the mixture was extracted with 3 portions of 20 mL toluene. The toluene portions were combined and washed with 50 mL of an aqueous saturated sodium hydrogen carbonate solution and then dried over magnesium sulfate. The toluene solution was filtered and then analyzed by high performance liquid chromatography (absolute quantitative analysis). It was confirmed that the following products were produced:

4,4-dimethyl-3-oxopentanenitrile (desired product):
7.22 g (yield: 58%)
3-oxobutyronitrile (by-product):
0.04 g (0.55 wt. % of the desired product)
Compound having pyrimidine nucleus (by-product):
0.13 g (1.8 wt. % of the desired product).

The filtered toluene solution was concentrated under reduced pressure to give 7.63 g (isolation yield: 58%) of 4,4-dimethyl-3-oxopentanenitrile (purity: 94.6%, according to area percentage determined by high performance liquid chromatography) as pale yellow liquid.

EXAMPLE 4

Preparation of 3-cyclopropyl-3-oxopropio-nitrile

In a glass flask (inner volume: 500 mL) equipped with a stirrer, a thermometer, a dropping funnel and a reflux condenser were placed 40.5 g (0.75 mol) of sodium methoxide, 50.0 g (0.50 mol) of methyl cyclopropanecarboxylate, 30.8 g (0.75 mol) of acetonitrile, and 50 g of dimethyl sulfoxide (relative dielectric constant at 20° C.: 48.9) under nitrogen atmosphere. The mixture was heated under reflux at 82° C. for 6 hours. After the reaction was complete, the reaction mixture was analyzed by high performance liquid chromatography (absolute quantitative analysis). It was confirmed that the following products were produced:

3-cyclopropyl-3-oxopropionitrile (desired product):
47.5 g (yield: 87%)
3-oxobutyronitrile (by-product):
0.65 g (1.4 wt. % of the desired product)
Compound having pyrimidine nucleus (by-product):
0.36 g (0.76 wt. % of the desired product).

Subsequently, 400 mL of toluene was added to the reaction mixture. To the mixture was dropwise added 100 mL of water under stirring, keeping the temperature of the mixture at 30° C. or lower. Thus produced aqueous portion was taken out.

Subsequently, to the aqueous portion was added 70 mL (0.84 mol) of hydrochloric acid (12 mol/L), while chilling the aqueous portion in an ice bath. After the aqueous solution became to have pH 7.0, the solution was subjected to extraction using three portions of 100 mL toluene. The toluene portions were combined and washed with 30 mL of an aqueous saturated sodium hydrogen carbonate solution and then dried over magnesium sulfate. The toluene solution was filtered and then analyzed by high performance liquid chromatography (absolute quantitative analysis). It was confirmed that the following products were produced:

3-cyclopropyl-3-oxopropionitrile (desired product):
45.4 g (yield: 83%)
3-oxobutyronitrile (by-product):
0.15 g (0.33 wt. % of the desired product)
Compound having pyrimidine nucleus (by-product):
0.04 g (0.09 wt. % of the desired product).

EXAMPLE 5

Preparation of 3-cyclopropyl-3-oxopropio-nitrile

The procedures of Example 4 were repeated except that dimethyl sulfoxide (aprotic polar organic solvent) was replaced with N,N'-dimethylimidazolidinone (relative dielectric constant at 25° C.: 37.6). The reaction was carried out in the manner as described in Example 1.

After the reaction was complete, the reaction mixture was analyzed by high performance liquid chromatography (absolute quantitative analysis). It was confirmed that the following products were produced:
3-cyclopropyl-3-oxopropionitrile (desired product):
47.2 g (yield: 87%)
3-oxobutyronitrile (by-product):
0.53 g (1.1 wt. % of the desired product)
Compound having pyrimidine nucleus (by-product):
0.60 g (1.3 wt. % of the desired product).

Subsequently, the step of phase separation and step of neutralization-extraction were carried out in the manner as described in Example 1. After these steps were complete, the reaction mixture was analyzed by high performance liquid chromatography (absolute quantitative analysis). It was confirmed that the following products were produced:
3-cyclopropyl-3-oxopropionitrile (desired product):
45.3 g (yield: 83%)
3-oxobutyronitrile (by-product):
0.04 g (0.09 wt. % of the desired product)
Compound having pyrimidine nucleus (by-product):
0.15 g (0.33 wt. % of the desired product).

REFERENCE EXAMPLE 3

Preparation of 3-cyclopropyl-3-oxopropionitrile (with No Phase Separation Step)

In the reaction apparatus described in Example 4 were placed 40.5 g (0.75 mol) of sodium methoxide, 50.0 g (0.50 mol) of methyl cyclopropanecarboxylate, 30.8 g (0.75 mol) of acetonitrile, and 50 g of dimethyl sulfoxide (relative dielectric constant at 20° C.: 48.9) under nitrogen atmosphere. The mixture was heated under reflux at 82° C. for 6 hours. After the reaction was complete, the reaction mixture was analyzed by high performance liquid chromatography (absolute quantitative analysis). It was confirmed that the following products were produced:
3-cyclopropyl-3-oxopropionitrile (desired product):
47.1 g (yield: 86%)
3-oxobutyronitrile (by-product):
0.44 g (0.93 wt. % of the desired product)
Compound having pyrimidine nucleus (by-product):
0.41 g (0.87 wt. % of the desired product).

Subsequently, 400 mL of toluene was added to the reaction mixture. To the mixture were added 56.7 mL (0.68 mol) of hydrochloric acid (12 mol/L) and 100 mL of water, keeping the temperature of the mixture at 30° C. or lower. After the aqueous solution became to have pH 2.0, the solution was subjected to extraction using three portions of 100 mL toluene. The toluene portions were combined and washed with 30 mL of an aqueous saturated sodium hydrogen carbonate solution and then dried over magnesium sulfate. The toluene solution was filtered and analyzed by high performance liquid chromatography (absolute quantitative analysis). It was confirmed that the following products were produced:
3-cyclopropyl-3-oxopropionitrile (desired product):
44.2 g (yield: 81%)
3-oxobutyronitrile (by-product):
0.16 g (0.36 wt. % of the desired product)
Compound having pyrimidine nucleus (by-product):
0.40 g (0.90 wt. % of the desired product).

EXAMPLE 6

Preparation of 4-methyl-3-oxopentanenitrile

In the reaction apparatus described in Example 4 were placed 40.5 g (0.75 mol) of sodium methoxide, 51.1 g (0.50 mol) of methyl isobutylate, 30.8 g (0.75 mol) of acetonitrile, and 51 g of dimethyl sulfoxide (relative dielectric constant at 20° C.: 48.9) under nitrogen atmosphere. The mixture was heated under reflux at 82° C. for 6 hours. After the reaction was complete, the resulting mixture was cooled to room temperature. The cooled reaction mixture was analyzed by high performance liquid chromatography (absolute quantitative analysis). It was confirmed that the following products were produced:
4-methyl-3-oxopentanenitrile (desired product):
46.1 g (yield: 83%)
3-oxobutyronitrile (by-product):
0.23 g (0.50 wt. % of the desired product)
Compound having pyrimidine nucleus (by-product):
0.41 g (0.89 wt. % of the desired product).

Subsequently, 100 mL of toluene was added to the reaction mixture, and the mixture was cooled to room temperature. To the mixture was dropwise added 100 mL of water under stirring, keeping the temperature of the mixture at 30° C. or lower. Thus produced aqueous portion was taken out.

Subsequently, to the aqueous portion was added 56.5 mL (0.68 mol) of hydrochloric acid (12 mol/L), while chilling the aqueous portion in an ice bath. After the aqueous solution became to have pH 7.0, the solution was subjected to extraction using three portions of 100 mL toluene. The toluene portions were combined and washed with 30 mL of an aqueous saturated sodium hydrogen carbonate solution and then dried over magnesium sulfate. The toluene solution was filtered and then analyzed by high performance liquid chromatography (absolute quantitative analysis). It was confirmed that the following products were produced:
4-methyl-3-oxopentanenitrile (desired product):
43.9 g (yield: 79%)
3-oxobutyronitrile (by-product):
0.14 g (0.32 wt. % of the desired product)
Compound having pyrimidine nucleus (by-product):
0.06 g (0.14 wt. % of the desired product).

EXAMPLE 7

Preparation of 4,4-dimethyl-3-oxopentane-nitrile

In a glass flask (inner volume: 100 mL) equipped with a stirrer, a thermometer, a dropping funnel and a reflux condenser were placed 8.10 g (0.15 mol) of sodium methoxide, 11.62 g (0.1 mol) of methyl pivalate, 6.15 g (0.15 mol) of acetonitrile, and 11.62 g of dimethyl sulfoxide (relative dielectric constant at 20° C.: 48.9) under nitrogen atmosphere. The mixture was heated under reflux at 82° C. for 6 hours. After the reaction was complete, 23 mL of toluene was added to the reaction mixture, and the resulting mixture was cooled to room temperature. To the cooled mixture was dropwise added 23 mL of water under stirring, keeping the temperature of the mixture at 30° C. or lower. Thus produced aqueous portion was taken out.

Subsequently, to the aqueous portion was added 14 mL (0.17 mol) of hydrochloric acid (12 mol/L), while chilling the aqueous portion in an ice bath. After the aqueous solution became to have pH 7.0, the solution was subjected to extraction using three portions of 30 mL toluene. The toluene portions were combined and washed with 30 mL of an aqueous saturated sodium hydrogen carbonate solution and then dried over magnesium sulfate. The toluene solution was filtered and then analyzed by high performance liquid chromatography (absolute quantitative analysis). It was confirmed that the following products were produced:
4,4-dimethyl-3-oxopentanenitrile (desired product):
9.76 g (yield: 78%)
3-oxobutyronitrile (by-product):
0.03 g (0.31 wt. % of the desired product)
Compound having pyrimidine nucleus (by-product):
0.01 g (0.10 wt. % of the desired product).

REFERENCE EXAMPLE 4

Preparation of 4,4-dimethyl-3-oxopentanenitrile (with No Phase Separation Step)

In the reaction apparatus described in Example 4 were placed 40.5 g (0.75 mol) of sodium methoxide, 58.1 g (0.50 mol) of methyl pivalate, 30.8 g (0.75 mol) of acetonitrile, and 58.1 g of dimethyl sulfoxide (relative dielectric constant at 20° C.: 48.9) under nitrogen atmosphere. The mixture was heated under reflux at 82° C. for 6 hours. After the reaction was complete, 400 mL of toluene was added to the reaction mixture. To the mixture were added 56.7 mL (0.68 mol) of hydrochloric acid (12 mol/L) and 100 mL of water, keeping the temperature of the resulting mixture at 30° C. or lower. After the reaction mixture became to have pH 2.0, the mixture was extracted with 3 portions of 100 mL toluene. The toluene portions were combined and washed with 30 mL of an aqueous saturated sodium hydrogen carbonate solution and then dried over magnesium sulfate. The toluene solution was filtered and then analyzed by high performance liquid chromatography (absolute quantitative analysis). It was confirmed that the following products were produced:
4,4-dimethyl-3-oxopentanenitrile (desired product):
48.7 g (yield: 78%)
3-oxobutyronitrile (by-product):
0.20 g (0.42 wt. % of the desired product)
Compound having pyrimidine nucleus (by-product):
0.28 g (0.57 wt. % of the desired product).

EXAMPLE 8

Preparation of 3-oxopentanenitrile

In the reaction apparatus described in Example 7 were placed 8.10 g (0.15 mol) of sodium methoxide, 8.81 g (0.10 mol) of methyl propionate, 6.15 g (0.15 mol) of acetonitrile, and 11.62 g of dimethyl sulfoxide (relative dielectric constant at 20° C.: 48.9) under nitrogen atmosphere. The mixture was heated under reflux at 82° C. for 6 hours. After the reaction was complete, to the resulting mixture was added 20 mL of toluene, and the mixture was cooled to room temperature. To the mixture were dropwise added 20 mL of water under stirring, keeping the temperature of the resulting mixture at 30° C. or lower. The aqueous portion was then taken out.
To the aqueous portion was added 14 mL (0.17 mol) of hydrochloric acid (12 mol/L), while chilling the aqueous portion in an ice bath. After the aqueous solution became to have pH 7.0, the solution was subjected to extraction using three portions of 20 mL toluene. The toluene portions were combined and washed with 30 mL of an aqueous saturated sodium hydrogen carbonate solution and then dried over magnesium sulfate. The toluene solution was filtered and then analyzed by high performance liquid chromatography (absolute quantitative analysis). It was confirmed that the following products were produced
3-oxopentanenitrile (desired product):
6.11 g (yield: 63%)
3-oxobutyronitrile (by-product):
0.03 g (0.49 wt. % of the desired product)
Compound having pyrimidine nucleus (by-product):
0.01 g (0.16 wt. % of the desired product).

EXAMPLE 9

Preparation of 4-phenyl-3-oxobutyronitrile

In the reaction apparatus described in Example 7 were placed 8.10 g (0.15 mol) of sodium methoxide, 15.02 g (0.10 mol) of methyl phenylacetate, 6.15 g (0.15 mol) of acetonitrile, and 15.02 g of dimethyl sulfoxide (relative electric constant at 20° C.: 48.9) under nitrogen atmosphere. The mixture was heated under reflux at 82° C. for 4 hours. After the reaction was complete, to the resulting mixture was added 30 mL of toluene, and the mixture was cooled to room temperature. To the mixture were dropwise added 50 mL of water under stirring, keeping the temperature of the resulting mixture at 30° C. or lower. The aqueous portion was then taken out.
To the aqueous portion was added 14 mL (0.17 mol) of hydrochloric acid (12 mol/L), while chilling the aqueous portion in an ice bath. After the aqueous solution became to have pH 7.0, the solution was subjected to extraction using three portions of 30 mL toluene. The toluene portions were combined and washed with 30 mL of an aqueous saturated sodium hydrogen carbonate solution and then dried over magnesium sulfate. The toluene solution was filtered and then analyzed by high performance liquid chromatography (absolute quantitative analysis). It was confirmed that the following products were produced:
4-phenyl-3-oxobutyronitrile (desired product):
11.11 g (yield: 70%)
3-oxobutyronitrile (by-product):
0.03 g (0.27 wt. % of the desired product)
Compound having pyrimidine nucleus (by-product):
0.01 g (0.09 wt. % of the desired product).

INDUSTRIAL APPLICABILITY

By utilizing the present invention, a β-ketonitrile compound of a high purity can be obtained in a high yield and with simple procedures from an easily available aliphatic carboxylic acid ester compound and acetonitrile.

The invention claimed is:
1. A process for producing a β-ketonitrile compound having the formula (3):

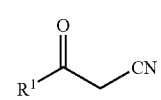

in which $R^1$ represents an aliphatic group which comprises the steps of:
(A) reacting an aliphatic carboxylic acid ester compound having the formula (1):

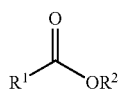

in which $R^1$ has the same meaning as above, and $R^2$ is a hydrocarbyl group, with acetonitrile in the presence of a metal alkoxide having a metal atom of X to give a reaction mixture containing a metal salt of a β-ketonitrile compound having the formula (2):

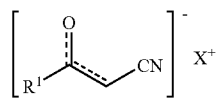

in which $R^1$ and X have the same meanings as above;

(B) adding a water-immiscible organic solvent and water to the reaction mixture, mixing them, and separating the aqueous solution containing the metal salt of β-ketonitrile compound; and (C) neutralizing the aqueous solution containing the metal salt of β-ketonitrile compound by addition of an acid and extracting a free β-ketonitrile compound with an organic solvent.

2. The process of claim 1, wherein the step of reacting an aliphatic carboxylic acid ester compound and acetonitrile in the presence of a metal alkoxide is performed in the presence of a aprotic polar organic solvent.

3. The process of claim 2, wherein the aprotic polar organic solvent is an organic solvent having a relative dielectric constant in the range of 30 to 50 at a temperature range of 20 to 25° C.

4. The process of claim 3, wherein the aprotic polar organic solvent having a relative dielectric constant in the range of 30 to 50 at a temperature range of 20 to 25° C. is dimethyl sulfoxide or N,N'-dimethyl-imidazolidinone.

5. The process of claim 1, wherein the acetonitrile is employed in an amount of 1.1 to 2.5 moles per one mole of the aliphatic carboxylic acid ester compound.

6. The process of claim 1, wherein the step of reacting an aliphatic carboxylic acid ester compound and acetonitrile in the presence of a metal alkoxide is performed at a temperature in the range of 50 to 110° C.

7. The process of claim 1, wherein the separating step (B) comprises procedures of adding to the reaction mixture the water-immiscible organic solvent and water and then stirring the resulting mixture with addition of water.

8. The process of claim 1, wherein the neutralization of the step (C) is performed by adding an acid to the aqueous solution containing the metal salt of β-ketonitrile compound to give an aqueous solution of pH 6 to 10.

* * * * *